(12) United States Patent
Friedhoff

(10) Patent No.: US 9,345,711 B2
(45) Date of Patent: *May 24, 2016

(54) METHODS FOR ACUTE AND LONG-TERM TREATMENT OF DRUG ADDICTION

(71) Applicant: DemeRx, Inc., Fort Lauderdale, FL (US)

(72) Inventor: Lawrence Friedhoff, Fort Lauderdale, FL (US)

(73) Assignee: DEMERX, INC., Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/195,822

(22) Filed: Mar. 3, 2014

(65) Prior Publication Data

US 2015/0231145 A1    Aug. 20, 2015

Related U.S. Application Data

(63) Continuation of application No. PCT/US2014/019692, filed on Feb. 28, 2014.

(60) Provisional application No. 61/941,387, filed on Feb. 18, 2014, provisional application No. 61/945,746, filed on Feb. 27, 2014.

(51) Int. Cl.
*A61K 31/55* (2006.01)
*A61K 31/407* (2006.01)

(52) U.S. Cl.
CPC ............... *A61K 31/55* (2013.01); *A61K 31/407* (2013.01)

(58) Field of Classification Search
CPC ............................. A61K 31/407; A61K 31/55
See application file for complete search history.

(56) References Cited

U.S. PATENT DOCUMENTS

| | | |
|---|---|---|
| 4,626,539 A | 12/1986 | Aungst et al. |
| 4,806,341 A | 2/1989 | Chien et al. |
| 5,149,538 A | 9/1992 | Granger et al. |
| 5,591,738 A | 1/1997 | Lotsof |
| 6,348,456 B1 | 2/2002 | Mash et al. |
| 6,933,308 B2 | 8/2005 | Boy et al. |
| 7,220,737 B1 | 5/2007 | Mash |
| 8,362,007 B1 | 1/2013 | Mash et al. |
| 9,045,481 B2 | 6/2015 | Mash et al. |
| 2003/0153552 A1 | 8/2003 | Mash et al. |
| 2003/0194438 A1 | 10/2003 | Prescott et al. |
| 2010/0311722 A1 | 12/2010 | Mash |
| 2012/0083485 A1 | 4/2012 | Mash |
| 2012/0253037 A1 | 10/2012 | Moriarty et al. |
| 2013/0165647 A1 | 6/2013 | Moriarty et al. |
| 2013/0303756 A1 | 11/2013 | Mash et al. |
| 2015/0231147 A1 | 8/2015 | Friedhoff |

FOREIGN PATENT DOCUMENTS

| | | |
|---|---|---|
| GB | 2 271 059 | 4/1994 |
| WO | WO-99/11250 | 3/1999 |
| WO | WO 9911250 A2 * | 3/1999 |
| WO | WO-2013/040471 | 3/2013 |

OTHER PUBLICATIONS

Weiss, Current Opinion in Pharmacology, 2005, Elsevier, vol. 5, pp. 9-19.*
Khan et. al., American Heart Journal, 2002, Mosby Inc., vol. 143, No. 1, pp. 7-14.*
Krantz et. al., Annals of Internal Medicine, 2009, American College of Physicians, vol. 150, pp. 387-395.*
U.S. Appl. No. 13/593,454, filed Aug. 23, 2012, Moriarty et al.
U.S. Appl. No. 14/195,822, filed Mar. 3, 2014, Lawrence Friedhoff.
Australian New Zealand Clinical Trials Registry ACTRN12612000821897, 2012.
U.S. Appl. No. 14/214,157, filed Mar. 14, 2014, Friedhoff, Lawrence.
U.S. Appl. No. 14/292,632, filed May 30, 2014, Friedhoff, Lawrence.
U.S. Appl. No. 14/295,273, filed Jun. 3, 2014, Friedhoff, Lawrence.
U.S. Appl. No. 14/298,534, filed Jun. 6, 2014, Mash et al.
U.S. Appl. No. 14/346,655, filed Mar. 14, 2014, Friedhoff, Lawrence.
Calsyn et al., "Slow tapering from methadone maintenance in a program encouraging indefinite maintenance," Journal of Substance Abuse Treatment, (2006), 30:159-163.
Donnelly, J.R., "The Need for Ibogaine in Drug and Alcohol Addiction Treatment," Journal of Legal Medicine, (2011), 32:93-114.
Eap et al., "Interindividual Variability of the Clinical Pharmacokinetics of Methadone," Clinical Pharmacokinetics, (2002), 41(14):1153-1193.
Huffman et al., "A formal Synthesis of (±)-Ibogamine," J. Org. Chem., 1985, 50:1460-1464.
Mash, et al. "Ibogaine in the Treatment of Heroin Withdrawal," The Alkaloids 56, 2001, pp. 1-17.
Mitchell et al., "Temperature and the cold pressor test", J. Pain, 2004, 5:233-237.
Pearl et al., "Radioligand-binding Study of Noribogaine, A Likely Metabolite of Ibogaine", Brain Research, 1995, 675:342-344.
Khan et al., "Long QT syndrome: Diagnosis and management", American Heart Journal, 2002, 143(1):7-14.
PCT International Search Report and Written Opinion dated Mar. 10, 2014 in related PCT Patent Application No. PCT/US13/69235.
Jaffe, "Drug Addiction and Drug Abuse", Goodman and Gillman's The Pharmacological Basis of Therapeutics, 8th ed., date unknown, pp. 522-523; pp. 559-568.
International Preliminary Report on Patentability for PCT/US2013/069235, mailed Sep. 15, 2005.
PCT International Preliminary Report on Patentability dated Sep. 24, 2015 for PCT Application No. PCT/US2014/028946.

(Continued)

*Primary Examiner* — Sarah Pihonak
(74) *Attorney, Agent, or Firm* — Foley & Lardner LLP

(57) ABSTRACT

This invention is directed to a method of treating opioid or opioid-like drug addiction, including acute and post-acute withdrawal symptoms, comprising treating an addicted patient with noribogaine at a dosage that provides an average serum concentration of about 50 ng/mL to about 850 ng/mL (AUC/24 h) under conditions where the QT interval prolongation does not exceed about 50 milliseconds.

16 Claims, 5 Drawing Sheets

(56) References Cited

OTHER PUBLICATIONS

PCT International Search Report and Written Opinion for Appl No. PCT/US2015/016186 dated Apr. 24, 2015 5 Pages.
Stichering, Christian, Methadone-induced Torsade de pointes tachycardias, Swiss Med Wkly, 2005; vol. 135, pp. 282-285.
International Search Report and Written Opinion Application No. PCT/US2015/062783, mail date Feb. 9, 2016, 16 pages.
PCT International Preliminary Report on Patentability for PCT Patent Application No. PCT/US14/19692, dated Feb. 1, 2016. 19 pages.
Popik et. al. "100 Years of Ibogaine: Neourochemical and Pharmacological Actions of a Putative Anti-addictive Drug." Pharmacological Reviews (1995)47:235:253.
Sharma et. al. "Enhancement of Morphine Antinociception by Ibogaine and Noribogaine in Morphine-tolerant Mice," Pharmacology (1998) 57:229-232.

* cited by examiner

METHODS FOR ACUTE AND LONG-TERM TREATMENT OF DRUG ADDICTION

CROSS-REFERENCE TO RELATED APPLICATIONS

This application is a Continuation of International Application No. PCT/US14/19692, filed Feb. 28, 2014, and claims priority under 35 U.S.C. section 119(e) of U.S. Provisional Application No. 61/945,746, filed on Feb. 27, 2014 and, U.S. Provisional Application No. 61/941,387, filed on Feb. 18, 2014, all of which are incorporated in their entirety herein by reference.

FIELD OF THE INVENTION

This invention is directed to a method of treating addiction to an opioid or opioid-like drug, including acute and post-acute withdrawal symptoms, comprising treating an opioid-addicted patient with noribogaine at a dosage that provides an average serum concentration of about 50 ng/mL to about 850 ng/mL (AUC/24 h), including under conditions where the QT interval prolongation does not exceed about 50 milliseconds.

STATE OF THE ART

Substance addiction is a serious public health problem throughout the world. Heroin and other opioids, including prescription painkillers, are widely abused and account for a large percentage of illicit drug use. Opioid use is also linked to approximately 50% of violent crimes in the United States and costs the U.S. economy billions of dollars per year.

Acute withdrawal from drug dependence is characterized by dramatic and traumatic symptoms, including sweating, racing heart, palpitations, muscle tension, tightness in the chest, difficulty breathing, tremor, nausea, vomiting, diarrhea, grand mal seizures, heart attacks, strokes, hallucinations and delirium tremens (DTs). Once acute withdrawal symptoms have subsided, post-acute withdrawal syndrome can last for months or years. Post-acute withdrawal symptoms include fatigue, depression, lack of motivation, and increased pain sensitivity.

Numerous treatments have been developed in attempts to ameliorate acute and post-acute withdrawal symptoms. However, in most cases, treatment of withdrawal requires use of other addictive substances (e.g., morphine or methadone). Treatment also requires that the addict attend a clinic daily for an extended amount of time. Due to the severity and duration of withdrawal symptoms, opioid-addicted patients have a high rate of relapse. There is a significant need for effective, non-addictive treatment for acute and post-acute opioid withdrawal symptoms.

While the prior art suggests that ibogaine at higher doses is useful as a treatment for addiction, use of ibogaine is associated with hallucinations and other negative side effects. In the United States, ibogaine is classified as a Schedule I controlled substance.

Noribogaine is a metabolite of ibogaine found in human, dog, rat and monkey. Noribogaine compounds have been suggested to have a greater and longer lasting activity in humans than ibogaine for reducing craving for addictive substances and treating chemical dependency. U.S. Pat. No. 6,348,456, incorporated by reference herein in its entirety, discloses highly purified noribogaine and teaches that it should be provided at dosages from about 0.01 to about 100 mg per kg body weight per day to treat addiction, although no human data was provided showing an effective dose to treat opioid or opioid-like drug addiction.

The therapeutic dosing of noribogaine for treating opioid or opioid-like drug addiction in humans has not previously been addressed, especially as it relates to dosing protocols that are effective, as well as safe. Indeed, prior to the instant invention, it was uncertain as to whether noribogaine could be administered at a dose which was therapeutic while at the same time safe for patients.

SUMMARY

While noribogaine has been disclosed for treatment of substance addiction, its use in humans is complicated by the fact that the ranges in the prior art are exceptionally broad (0.01 to 1000 mg/kg body weight). Furthermore, human clinical studies demonstrate that the lower dosing of noribogaine has minimal impact on withdrawal symptoms in addicted patients. Thus, the previously disclosed broad range has now been found to be insufficient for human therapy at the lower end of this range.

Moreover, the use of noribogaine imparts a dose dependent prolongation of the treated patient's QT interval, rendering higher dosing of noribogaine unacceptable. A prolonged QT interval is a marker of potential ventricular tachyarrhythmia which, and can result in death. For reasons that are not apparent, this prolongation increases in opioid addicted patients as compared to healthy individuals.

The current invention is predicated on the surprising discovery that treatment with a narrow dosage range of noribogaine or pharmaceutically acceptable salt or solvate thereof, between greater than about 1 mg/kg body weight and about 8 mg/kg body weight, provides a therapeutic reduction in withdrawal symptoms and/or an increase in time to resumption of opioid use in opioid-addicted patients. Preferably, the dose range that provide both therapeutic results and an acceptable QT interval prolongation of less than 50 milliseconds in opioid and opioid-like drug addicted humans is between about 1.3 mg per kg body weight and no more than about 4 mg per kg body weight and, more preferably between about 1.3 mg per kg body weight and no more than about 3 mg per kg body weight, or any subrange or subvalue within the aforementioned ranges. Opioid-like drugs, including cocaine, ketamine, and methamphetamine, are not opioids but act through the opioid receptors, and thus addiction to these drugs also can be treated with noribogaine.

In a preferred embodiment, the narrow therapeutic doses of noribogaine or pharmaceutically acceptable salt or solvate described above unexpectedly do not prolong the QT interval to unacceptable levels in human addicted patients. It is expected that opioid or opioid-like drug addicted patients will be administered therapeutic doses of noribogaine or pharmaceutically acceptable salt or solvate thereof in a clinical setting with cardiac monitoring. In some embodiments, the patient will be pre-screened to evaluate tolerance for prolongation of QT interval, e.g., to determine whether the patient has any pre-existing cardiac conditions which would disqualify them from treatment with noribogaine.

Some aspects of the current invention are further predicated on the discovery that even lower doses of noribogaine or pharmaceutically acceptable salt or solvate thereof, for example approximately 80% or less of the therapeutic dose, may be effective for prevention of relapse of opioid (or opioid-like drug) use in an opioid-addicted patient treated to ameliorate their opioid use. That is, a lower dose of noribogaine can prevent a patient who is no longer physically addicted to opioid from relapsing to opioid use. Without being bound by theory, it is believed that a patient who is no longer physically addicted to opioids or opioid-like drug requires less noribogaine to prevent relapse because the opioid or opioid-like drug does not compete with noribogaine for receptor binding, and/or because desensitization of one or more receptors in the brain by the opioid or opioid-like drug is reversed when the patient ceases to take the drug. This lower, maintenance dose of noribogaine results in a QT interval prolongation that does not require clinical cardiac monitoring.

In some embodiments, the therapeutic dose of noribogaine or pharmaceutically acceptable salt or solvate thereof administered to the patient is sufficient to provide an average serum concentration of about 50 ng/mL to about 850 ng/mL (area under the curve/24 hours, AUC/24 h), or any subrange or subvalue there between. In a preferred embodiment, the dose of noribogaine or pharmaceutically acceptable salt or solvate thereof administered to the patient provides an average serum concentration of about 50 ng/mL to about 400 ng/mL (AUC/24 h).

In some embodiments, the patient is administered a high (therapeutic) dose of noribogaine or pharmaceutically acceptable salt or solvate thereof for a period of time to ameliorate the most significant withdraw symptoms, and then is administered a lower (maintenance) dose to prevent relapse to opioid or opioid-like drug use. In some embodiments, the patient is administered a therapeutic dose of noribogaine or pharmaceutically acceptable salt or solvate thereof for a period of time to ameliorate the most significant withdraw symptoms, and then is administered a decreasing (tapered) amount of noribogaine or pharmaceutically acceptable salt or solvate thereof over time until the maintenance dose is reached. In some embodiments, a high initial therapeutic dose is administered, followed by administration of a lower therapeutic dose. In some embodiments, the dose of noribogaine is tapered over time from the high therapeutic dose to a lower therapeutic dose.

In some embodiments, the dose of noribogaine or pharmaceutically acceptable salt or solvate thereof that provides an average serum concentration of about 50 ng/mL to about 850 ng/mL (AUC/24 h) is administered as a single dose. In some embodiments, the dose of noribogaine or pharmaceutically acceptable salt or solvate thereof that provides an average serum concentration of about 50 ng/mL to about 850 ng/mL (AUC/24 h) is administered as multiple doses. In some embodiments, the aggregate dose of noribogaine or pharmaceutically acceptable salt or solvate thereof is from greater than about 1 mg/kg to about 8 mg/kg. In a preferred embodiment, the aggregate dose of noribogaine or pharmaceutically acceptable salt or solvate thereof is from greater than about 1 mg/kg to about 4 mg/kg. In another preferred embodiment, the aggregate dose of noribogaine or pharmaceutically acceptable salt or solvate thereof is from greater than about 1 mg/kg to 3 mg/kg.

In some embodiments, the serum concentration is sufficient to inhibit or ameliorate said abuse while maintaining a QT interval of less than 500 milliseconds (ms) during said treatment. In some embodiments, the therapeutic dose of noribogaine or pharmaceutically acceptable salt or solvate thereof provides prolongation of the QT interval of less than 80 ms. In a preferred embodiment, the maintenance dose of noribogaine or pharmaceutically acceptable salt or solvate thereof provides prolongation of the QT interval of less than 50 ms. In some embodiments, the maintenance dose or therapeutic dose of noribogaine or pharmaceutically acceptable salt or solvate thereof provides prolongation of the QT interval of less than 30 ms. In a preferred embodiment, the maintenance dose of noribogaine or pharmaceutically acceptable salt or solvate thereof provides prolongation of the QT interval of less than 20 ms. In one embodiment, the QT prolongation is equivalent to or less than that observed in patients receiving methadone treatment. In a preferred embodiment, the patient is tested to determine QT interval before treatment with noribogaine, and if clinician determines that the QT prolongation would be unacceptable risk, noribogaine therapy will be contraindicated.

DETAILED DESCRIPTION

Figure 1:
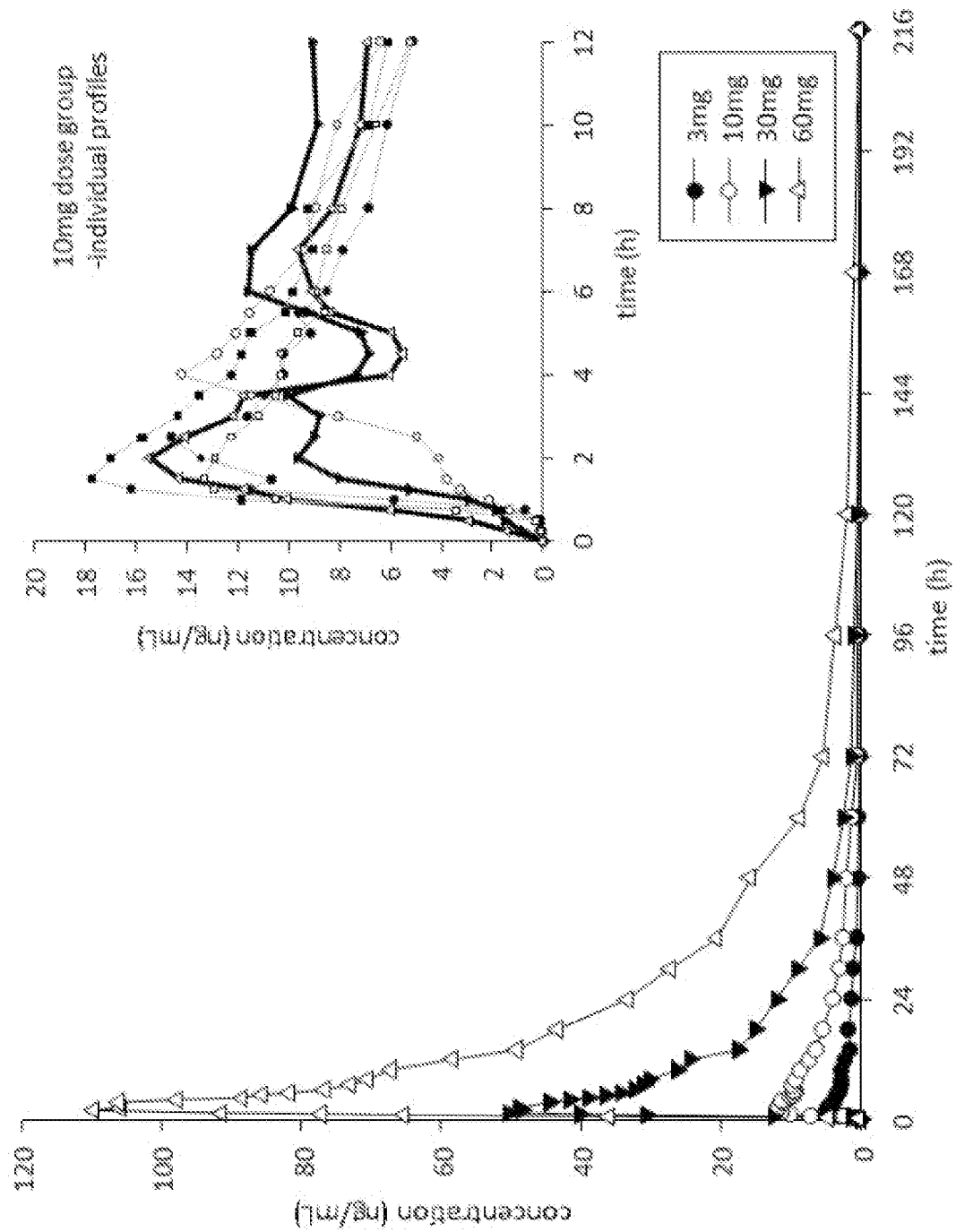
FIG. 1 represents mean noribogaine concentration-time profiles in healthy patients after single oral dosing with 3, 10, 30 or 60 mg doses. Inset: Individual concentration-time profiles from 0-12 h after a 10 mg dose.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a compound" includes a plurality of compounds.

I. DEFINITIONS

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 10%, 5% or 1%.

"Administration" refers to introducing an agent into a patient. Typically, an effective amount is administered, which amount can be determined by the treating physician or the like. Any route of administration, such as oral, topical, subcutaneous, peritoneal, intra-arterial, inhalation, vaginal, rectal, nasal, introduction into the cerebrospinal fluid, or instillation into body compartments can be used. The agent may be administered by direct blood stream delivery, e.g. sublingual, intranasal, or intrapulmonary administration.

The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient.

"Periodic administration" or "periodically administering" refers to multiple treatments that occur on a daily, weekly, or monthly basis. Periodic administration may also refer to administration of noribogaine or salt or solvate thereof one, two, three, or more times per day. Administration may be via transdermal patch, gum, lozenge, sublingual tablet, intranasal, intrapulmonary, oral administration, or other administration.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

"Noribogaine" refers to the compound:

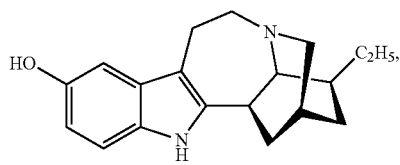

as well as noribogaine derivatives or pharmaceutically acceptable salts and pharmaceutically acceptable solvates thereof. It should be understood that where "noribogaine" is mentioned herein, one more polymorphs of noribogaine can be utilized and are contemplated. In some embodiments, noribogaine is noribogaine glucuronide. Noribogaine can be prepared by demethylation of naturally occurring ibogaine:

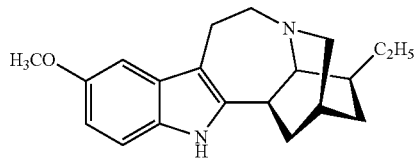

which is isolated from *Tabernanth iboga*, a shrub of West Africa. Demethylation may be accomplished by conventional techniques such as by reaction with boron tribromide/methylene chloride at room temperature followed by conventional purification. See, for example, Huffman, et al., J. Org. Chem. 50:1460 (1985), which incorporated herein by reference in its entirety. Noribogaine can be synthesized as described, for example in U.S. Patent Pub. Nos. 2013/0165647, 2013/0303756, and 2012/0253037, PCT Patent Publication No. WO 2013/040471 (includes description of making noribogaine polymorphs), and U.S. patent application Ser. No. 13/593,454, each of which is incorporated herein by reference in its entirety.

In some embodiments, the methods of the present disclosure entail the administration of a prodrug of noribogaine that provides the desired maximum serum concentrations and efficacious average noribogaine serum levels. A prodrug of noribogaine refers to a compound that metabolizes, in vivo, to noribogaine. In some embodiments, the prodrug is selected to be readily cleavable either by a cleavable linking arm or by cleavage of the prodrug entity that binds to noribogaine such that noribogaine is generated in vivo. In one preferred embodiment, the prodrug moiety is selected to facilitate binding to the μ and/or κ receptors in the brain either by facilitating passage across the blood brain barrier or by targeting brain receptors other than the μ and/or κ receptors. Examples of prodrugs of noribogaine are provided in U.S. patent application Ser. No. 13/165,626, the entire content of which is incorporated herein by reference.

This invention is not limited to any particular chemical form of noribogaine, and the drug may be given to patients either as a free base, solvate, or as a pharmaceutically acceptable acid addition salt. In the latter case, the hydrochloride salt is generally preferred, but other salts derived from organic or inorganic acids may also be used. Examples of such acids include, without limitation, those described below as "pharmaceutically acceptable salts" and the like.

"Pharmaceutically acceptable composition" refers to a composition that is suitable for administration to a human. Such compositions include various excipients, diluents, carriers, and such other inactive agents well known to the skilled artisan.

"Pharmaceutically acceptable salt" refers to pharmaceutically acceptable salts, including pharmaceutically acceptable partial salts, of a compound, which salts are derived from a variety of organic and inorganic counter ions well known in the art and include, by way of example only, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, oxalic acid and the like, and when the molecule contains an acidic functionality, include, by way of example only, sodium, potassium, calcium, magnesium, ammonium, tetraalkylammonium, and the like.

"Therapeutically effective amount" or "therapeutic amount" refers to an amount of a drug or an agent that, when administered to a patient suffering from a condition, will have the intended therapeutic effect, e.g., alleviation, amelioration, palliation or elimination of one or more manifestations of the condition in the patient. The therapeutically effective amount will vary depending upon the patient and the condition being treated, the weight and age of the subject, the severity of the condition, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of noribogaine, in the context of treating opioid or opioid-like drug dependency, refers to an amount of noribogaine that attenuates the dependency and/or symptoms of acute withdrawal for at least 2 hours beyond control (placebo), at least 5 hours beyond control, and preferably at least 10 hours beyond control.

A "therapeutic level" of a drug is an amount of noribogaine or pharmaceutical salt or solvate thereof that is sufficient to treat opioid or opioid-like drug addiction or to treat, prevent, or attenuate acute withdrawal symptoms, but not high enough to pose any significant risk to the patient. Therapeutic levels of drugs can be determined by tests that measure the actual concentration of the compound in the blood of the patient. This concentration is referred to as the "serum concentration."

As defined herein, a "maintenance amount" of a drug is an amount, typically less than the therapeutically effective amount that provides attenuation and/or prevention of post-acute withdrawal syndrome in a patient. The maintenance amount of the compound is expected to be less than the therapeutically effective amount because the level of inhibition does not need to be as high in a patient who is no longer physically addicted to opioid or opioid-like drug. For example, a maintenance amount is preferably 80%, 70%, 60%, 50%, 40%, 30%, 20%, or 10% less than a therapeutically effective amount, or any subvalue or subrange there between.

"Treatment," "treating," and "treat" are defined as acting upon a disease, disorder, or condition with an agent to reduce or ameliorate harmful or any other undesired effects of the disease, disorder, or condition and/or its symptoms. "Treatment," as used herein, covers the treatment of a human patient, and includes: (a) reducing the risk of occurrence of the condition in a patient determined to be predisposed to the condition but not yet diagnosed as having the condition, (b) impeding the development of the condition, and/or (c) relieving the condition, i.e., causing regression of the condition and/or relieving one or more symptoms of the condition. "Treating" or "treatment of" a condition or patient refers to taking steps to obtain beneficial or desired results, including clinical results such as the reduction of symptoms. For purposes of this invention, beneficial or desired clinical results include, but are not limited to: treating opioid or opioid-like drug addiction; treating, preventing, and/or attenuating acute withdrawal symptoms; treating, preventing, and/or attenuating long-term (post-acute) withdrawal symptoms; and preventing relapse of opioid or opioid-like drug use.

As used herein, the term "patient" refers to humans.

As used herein, the term "opiate" refers to naturally-occurring alkaloids found in the opium poppy. These include codeine, morphine, oripavine, pseudomorphine, and thebaine. Also included are opium, opium poppy, poppy straw, and extracts and concentrates thereof.

As used herein, the term "opioid" refers to naturally-occurring opiates and synthetic or semi-synthetic opioids that have psychoactive effects. Non-limiting examples include acetyl-alpha-methylphentanyl, acetylmethadol, alfentanil, allylprodine, alphacetylmethadol, alphamethadol, alpha-methylfentanyl, alpha-methylthiofentanyl, alphaprodine, anileridine, benzylmorphine, benzethidine, betacetylmethadol, beta-hydroxyfentanyl, beta-hydroxy-3-methylfentanyl, betameprodine, betacetylmethadol, beta-hydroxyfentanyl, beta-hydroxy-3-methylfentanyl, betameprodine, betamethadol, betaprodine, bezitramide, buprenorphine, butorphanol, carfentanil, clonitazene, codeine, desomorphine, dextromoramide, dextropropoxyphene, dezocine, diampromide, diamorphone, diethylthiambutene, dihydrocodeine, dihydroetorphine, dihydromorphine, dimenoxadol, dimepheptanol, dimethyl-thiambutene, dioxaphetyl butyrate, diphenoxylate, difenoxin, dipipanone, eptazocine, ethoheptazine, ethylmethylthiambutene, ethylmorphine, etonitazene, etorphine, etoxeridine, fentanyl, furethidine, heroin, hydrocodone, hydromorphone, hydroxypethidine, isomethadone, ketobemidone, levoalphacetylmethadol, levomethorphan, levorphanol, levophenacylmorphan, levomoramide, lofentanil, loperamide, laudanum, meperidine, meptazinol, metazocine, methadone, 3-methylfentanyl, 3-methylthiofentanyl, metopon, morphine, morpheridine, MPPP (1-methyl-4-phenyl-4-propionoxypiperidine), myrophine, narceine, nicomorphine, noracymethadol, norlevorphanol, normethadone, nalorphine, nalbuphene, normorphine, norpipanone, opium, oxycodone, oxymorphone, papaveretum, para-fluorofentanyl, paregoric, PEPAP (1-(-2-phenethyl)-4-phenyl-4-acetoxypiperidine), pentazocine, phenadoxone, phenampromide, phenomorphan, phenazocine, phenoperidine, piminodine, piritramide, propheptazine, promedol, properidine, propiram, propoxyphene, racemoramide, racemethorphan, racemorphan, remifentanil, sufentanil, tapentadol, thiofentanyl, tilidine, tramadol, trimeperidine, mixtures of any of the foregoing, salts of any of the foregoing, derivatives of any of the foregoing, and the like. The term opioids also encompasses opioid intermediates, including 4-cyano-2-dimethylamino-4,4-diphenyl butane, 2-methyl-3-morpholino-1,1-diphenylpropane-carboxylic acid, 4-cyano-1-methyl-4-phenylpiperidine, ethyl-4-phenylpiperidine-4-carboxylate, and 1-methyl-4-phenylpiperidine-4-carboxylic acid. Many opioids are Schedule I or Schedule II drugs in the US.

As used herein, the term "opioid-like drug" refers to any illicit drug that binds to one or more opioid receptor and causes opioid-like addiction. Acute and long-term withdrawal symptoms from cessation of use of such drugs may be similar to those from cessation of opioids. Opioid-like drugs include amphetamine, methamphetamine, ketamine, and cocaine.

As used herein, the term "QT interval" refers to the measure of the time between the start of the Q wave and the end of the T wave in the electrical cycle of the heart. Prolongation of the QT interval refers to an increase in the QT interval.

As used herein, the terms "addiction" and "dependence" are used interchangeably to refer to the patient's inability to stop using the opioid or opioid-like drug, even when it would be in his/her best interest to stop. The DSMIV-TR criteria for dependency include:

Dependence or significant impairment or distress, as manifested by 3 or more of the following during a 12 month period:
1. Tolerance or markedly increased amounts of the substance to achieve intoxication or desired effect or markedly diminished effect with continued use of the same amount of substance
2. Withdrawal symptoms or the use of certain substances to avoid withdrawal symptoms
3. Use of a substance in larger amounts or over a longer period than was intended
4. Persistent desire or unsuccessful efforts to cut down or control substance use
5. Involvement in chronic behavior to obtain the substance, use the substance, or recover from its effects
6. Reduction or abandonment of social, occupational or recreational activities because of substance use
7. Use of substances even though there is a persistent or recurrent physical or psychological problem that is likely to have been caused or exacerbated by the substance.

The term "solvate" as used herein refers to complexes with solvents in which noribogaine is reacted or from which noribogaine is precipitated or crystallized. For example, a complex with water is known as a "hydrate". Solvates of noribogaine are within the scope of the invention. It will be appreciated by those skilled in organic chemistry that many organic compounds can exist in more than one crystalline form. For example, crystalline form may vary based on the solvate used. Thus, all crystalline forms of noribogaine or the pharmaceutically acceptable solvates thereof are within the scope of the present invention.

II. METHODS OF THE INVENTION

As will be apparent to the skilled artisan upon reading this disclosure, the present invention provides a method for treating opioid or opioid-like drug, abuse including acute and post-acute withdrawal symptoms, in a patient addicted to opioid or opioid-like drug, comprising administering to the patient a dosage of noribogaine or pharmaceutically acceptable salt or solvate thereof.

Therapeutic Administration

In one aspect, this invention relates to treatment of acute withdrawal from an opioid or opioid-like drug in an addicted patient comprising administration of a therapeutically effective amount of noribogaine or pharmaceutically acceptable salt or solvate thereof.

In one aspect, this invention relates to a method for treating opioid or opioid-like drug abuse in an addicted patient, comprising administering to the patient a dosage of noribogaine or pharmaceutically acceptable salt or solvate thereof that provides an average serum concentration of about 50 ng/mL to about 850 ng/mL (AUC/24 h), said concentration being sufficient to inhibit or ameliorate said abuse while maintaining a QT interval of less than about 500 ms during said treatment.

In one aspect, this invention relates to a method for attenuating withdrawal symptoms in a human patient susceptible to such symptoms due to opioid or opioid-like drug addiction, comprising administering to the patient a dosage of noribogaine or pharmaceutically acceptable salt or solvate thereof that provides an average serum concentration of about 60 ng/mL to about 400 ng/mL (AUC/24 h), said concentration being sufficient to attenuate said symptoms while maintaining a QT interval of less than about 500 ms during said treatment. In some embodiments, the concentration is sufficient to attenuate said symptoms while maintaining a QT interval of less than about 470 ms during treatment. Preferably, the concentration is sufficient to attenuate said symptoms while maintaining a QT interval of less than about 450 ms during treatment. In one embodiment, the concentration is sufficient to attenuate said symptoms while maintaining a QT interval of less than about 420 ms during treatment. In one embodiment, the withdrawal symptoms are symptoms of acute withdrawal.

In one aspect, this invention relates to a method for attenuating withdrawal symptoms in a human patient susceptible to such symptoms due to opioid or opioid-like drug addiction, comprising administering to the patient a dosage of noribogaine or pharmaceutically acceptable salt or solvate thereof that provides an average serum concentration of about 50 ng/mL to about 400 ng/mL (AUC/24 h), said concentration being sufficient to attenuate said symptoms while maintaining a QT interval of less than about 500 ms during said treatment. In some embodiments, the concentration is sufficient to attenuate said symptoms while maintaining a QT interval of less than about 470 ms during treatment. Preferably, the concentration is sufficient to attenuate said symptoms while maintaining a QT interval of less than about 450 ms during treatment. In one embodiment, the concentration is sufficient to attenuate said symptoms while maintaining a QT interval of less than about 420 ms during treatment. In one embodiment, the withdrawal symptoms are symptoms of acute withdrawal.

In one embodiment, the average serum concentration of noribogaine is from about 50 ng/mL to about 800 ng/mL or about 60 ng/mL to about 800 ng/mL. In one embodiment, the average serum concentration of noribogaine is from about 50 ng/mL to about 700 ng/mL or about 60 ng/mL to about 700 ng/mL. In one embodiment, the average serum concentration of noribogaine is from about 50 ng/mL to about 600 ng/mL, or about 60 ng/mL to about 600 ng/mL. In a preferred embodiment, the average serum concentration of noribogaine is from about 50 ng/mL to about 500 ng/mL, or about 60 ng/mL to about 500 ng/mL. In one embodiment, the average serum concentration of noribogaine is from about 50 ng/mL to about 400 ng/mL, or about 60 ng/mL to about 400 ng/mL. In one embodiment, the average serum concentration of noribogaine is from about 50 ng/mL to about 300 ng/mL, or about 60 ng/mL to about 300 ng/mL. In one embodiment, the average serum concentration of noribogaine is from about 50 ng/mL to about 200 ng/mL, or about 60 ng/mL to about 200 ng/mL. In one embodiment, the average serum concentration of noribogaine is from about 50 ng/mL to about 100 ng/mL, or about 60 ng/mL to about 100 ng/mL. The ranges include both extremes as well as any subranges between.

In one embodiment, the dosage or aggregate dosage of noribogaine or salt or solvate thereof is from greater than about 1 mg/kg to about 8 mg/kg body weight per day. The aggregate dosage is the combined dosage, for example the total amount of noribogaine or pharmaceutically acceptable salt or solvate thereof administered over a 24-hour period where smaller amounts are administered more than once per day. In one embodiment, the dosage or aggregate dosage of noribogaine or salt or solvate thereof is from about 1.3 mg/kg to about 7 mg/kg body weight. In one embodiment, the dosage or aggregate dosage of noribogaine or salt or solvate thereof is from about 1.3 mg/kg to about 6 mg/kg body weight. In one embodiment, the dosage or aggregate dosage of noribogaine or salt or solvate thereof is from about 1.3 mg/kg to about 5 mg/kg body weight. In a preferred embodiment, the dosage or aggregate dosage of noribogaine or salt or solvate thereof is from about 1.3 mg/kg to about 4 mg/kg body weight. In one embodiment, the dosage or aggregate dosage of noribogaine or salt or solvate thereof is from about 1.3 mg/kg to about 3 mg/kg body weight. In one embodiment, the dosage or aggregate dosage of noribogaine or salt or solvate thereof is from about 1.3 mg/kg to about 2 mg/kg body weight. In one embodiment, the dosage or aggregate dosage of noribogaine or salt or solvate thereof is from about 1.5 mg/kg to about 3 mg/kg body weight. In one embodiment, the dosage or aggregate dosage of noribogaine or salt or solvate thereof is from about 1.7 mg/kg to about 3 mg/kg body weight. In one embodiment, the dosage or aggregate dosage of noribogaine or salt or solvate thereof is from about 2 mg/kg to about 4 mg/kg body weight. In one embodiment, the dosage or aggregate dosage of noribogaine or salt or solvate thereof is from about 2 mg/kg to about 3 mg/kg body weight. In one embodiment, the dosage or aggregate dosage of noribogaine or salt or solvate thereof is about 2 mg/kg body weight. The ranges include both extremes as well as any subranges there between.

In one embodiment, the dosage or aggregate dosage of noribogaine or salt or solvate thereof is about 8 mg/kg body weight per day. In one embodiment, the dosage or aggregate dosage of noribogaine or salt or solvate thereof is about 7 mg/kg body weight per day. In one embodiment, the dosage or aggregate dosage of noribogaine or salt or solvate thereof is about 6 mg/kg body weight per day. In one embodiment, the dosage or aggregate dosage of noribogaine or salt or solvate thereof is about 5 mg/kg body weight per day. In one embodiment, the dosage or aggregate dosage of noribogaine or salt or solvate thereof is about 4 mg/kg body weight per day. In one embodiment, the dosage or aggregate dosage of noribogaine or salt or solvate thereof is about 3 mg/kg body weight per day. In one embodiment, the dosage or aggregate dosage of noribogaine or salt or solvate thereof is about 2 mg/kg body weight per day. In one embodiment, the dosage or aggregate dosage of noribogaine or salt or solvate thereof is about 1.7 mg/kg body weight per day. In one embodiment, the dosage or aggregate dosage of noribogaine or salt or solvate thereof is about 1.5 mg/kg body weight per day. In one embodiment, the dosage or aggregate dosage of noribogaine or salt or solvate thereof is about 1.3 mg/kg body weight per day. In one embodiment, the dosage or aggregate dosage of noribogaine or salt or solvate thereof is about 1 mg/kg body weight per day.

In some embodiments, the therapeutic dose of noribogaine or salt or solvate thereof is a tapered dosing over a period of time, during which the patient is detoxified, for example, without suffering significant acute withdrawal symptoms. Without being bound by theory, it is believed that tapering will allow the full therapeutic effect of noribogaine with less prolongation of the QT interval. Tapering involves administration of one or more subsequently lower doses of noribogaine over time. For example, in some embodiments, the first tapered dose is about 50% to about 95% of the first or original dose. In some embodiments, the second tapered dose is about 40% to about 90% of the first or original dose. In some embodiments, the third tapered dose is about 30% to about 85% of the first or original dose. In some embodiments, the fourth tapered dose is about 20% to about 80% of the first or original dose. In some embodiments, the fifth tapered dose is about 10% to about 75% of the first or original dose.

In some embodiments, the first tapered dose is given after the first dose of noribogaine. In some embodiments, the first tapered dose is given after the second, third, or a subsequent dose of noribogaine. The first tapered dose may be administered at any time after the previous dose of noribogaine. The first tapered dose can be given once, for example, followed by subsequent further tapered doses, or it can be given multiple times with or without subsequent, further tapered doses (e.g., second, third, fourth, etc. tapered doses), which likewise can be given once or over multiple administrations, for example. In some embodiments, the first tapered dose is administered one hour, 6 hours, 12 hours, 18 hours, 24 hours, 36 hours, 48 hours, or more after the previous dose of noribogaine. Similarly, second, third, fourth, etc. tapered doses, if given, can be given one hour, 6 hours, 12 hours, 18 hours, 24 hours, 36 hours, 48 hours, or more after the previous dose of noribogaine.

In some embodiments, one tapered dose is given to achieve the desired lower therapeutic dose. In some embodiments, two tapered doses are given to achieve the desired lower therapeutic dose. In some embodiments, three tapered doses are given to achieve the desired lower therapeutic dose. In some embodiments, four or more tapered doses are given to achieve the desired lower therapeutic dose. Determination of the tapered doses, number of tapered doses, and the like can be readily made a qualified clinician.

In one embodiment, the QT interval is not prolonged more than about 50 ms. In one embodiment, the QT interval is not prolonged more than about 40 ms. In one embodiment, the QT interval is not prolonged more than about 30 ms. In one embodiment, the QT interval is not prolonged more than about 20 ms. In one embodiment, prolongation of the QT interval is equivalent to or less than the prolongation observed for methadone-treated patients.

In some embodiments, the patient is administered periodically, such as once, twice, three time, four times or five time daily with noribogaine or a pharmaceutically acceptable salt or solvate thereof. In some embodiments, the administration is once daily, or once every second day, once every third day, three times a week, twice a week, or once a week. The dosage and frequency of the administration depends on the route of administration, dosage, age and body weight of the patient, condition of the patient, without limitation. Determination of dosage and frequency suitable for the present technology can be readily made a qualified clinician.

Noribogaine or a pharmaceutically acceptable solvate or salt thereof, suitable for administration in accordance with the methods provide herein, can be suitable for a variety of delivery modes including, without limitation, oral and transdermal delivery. Compositions suitable for internal, pulmonary, rectal, nasal, vaginal, lingual, intravenous, intra-arterial, intramuscular, intraperitoneal, intracutaneous and subcutaneous routes may also be used. Possible dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A. Oslo editor, Easton Pa. 1980).

In a preferred embodiment, noribogaine or a pharmaceutically acceptable salt or solvate thereof is administered orally, which may conveniently be provided in tablet, caplet, sublingual, liquid or capsule form. In certain embodiments, the noribogaine is provided as noribogaine HCl, with dosages reported as the amount of free base noribogaine. In some embodiments, the noribogaine HCl is provided in hard gelatin capsules containing only noribogaine HCl with no excipients.

The patient may suffer from addiction to any opioid or opiate or opioid-like drug. In a preferred embodiment, the opioid or opioid-like drug is selected from the group consisting of heroin, cocaine, opiate, methadone, morphine, codeine, oxycodone, hydrocodone, and methamphetamine. In one embodiment, the opioid or opioid-like drug is heroin. In one embodiment, the opioid or opioid-like drug is methadone. In one embodiment, the opioid or opioid-like drug is morphine.

Maintenance Administration

In one aspect, this invention relates to treatment or attenuation of post-acute withdrawal from opioids or opioid-like drug in an addicted patient with a maintenance amount of noribogaine or pharmaceutically acceptable salt or solvate thereof.

In some aspects, this invention relates to a method to prevent relapse of opioid or opioid-like drug abuse in an addicted patient treated to ameliorate said abuse, said method comprising periodically administering to said patient a maintenance dosage of noribogaine.

In some embodiments, the patient undergoes long-term (e.g., one year or longer) treatment with maintenance doses of noribogaine or salt or solvate thereof. In some embodiments, the patient is treated for acute withdrawal with therapeutic doses of noribogaine as described above, and then the amount of noribogaine is reduced to maintenance levels after acute withdrawal symptoms would be expected to have subsided. Acute withdrawal symptoms generally are the most pronounced in the first 48 to 72 hours after cessation of the drug of addiction, although acute withdrawal may last as long as a week or more.

In some embodiments, the patient is administered a high (therapeutic) dose of noribogaine or pharmaceutically acceptable salt or solvate thereof for a period of time to ameliorate the most significant withdraw symptoms, and then is administered a lower (maintenance) dose to prevent relapse to opioid or opioid-like drug use. In some embodiments, the patient is administered a therapeutic dose of noribogaine or pharmaceutically acceptable salt or solvate thereof for a period of time to ameliorate the most significant withdraw symptoms, and then is administered a decreasing (tapered) amount of noribogaine or pharmaceutically acceptable salt or solvate thereof over time until the maintenance dose is reached.

In some embodiments, the maintenance dose of noribogaine or pharmaceutically acceptable salt or solvate thereof is 70% of the therapeutic dose. In some embodiments, the maintenance dose is 60% of the therapeutic dose. In some embodiments, the maintenance dose is 50% of the therapeutic dose. In some embodiments, the maintenance dose is 40% of the therapeutic dose. In some embodiments, the maintenance dose is 30% of the therapeutic dose. In some embodiments, the maintenance dose is 20% of the therapeutic dose. In some embodiments, the maintenance dose is 10% of the therapeutic dose.

In some embodiments, the maintenance average serum level of noribogaine is 70% of the therapeutic average serum level of noribogaine. In some embodiments, the maintenance average serum level of noribogaine is 60% of the therapeutic average serum level of noribogaine. In some embodiments, the maintenance average serum level of noribogaine is 50% of the therapeutic average serum level of noribogaine. In some embodiments, the maintenance average serum level of noribogaine is 40% of the therapeutic average serum level of noribogaine. In some embodiments, the maintenance average serum level of noribogaine is 30% of the therapeutic average serum level of noribogaine. In some embodiments, the maintenance average serum level of noribogaine is 20% of the therapeutic average serum level of noribogaine. In some embodiments, the maintenance average serum level of noribogaine is 10% of the therapeutic average serum level of noribogaine.

In one embodiment, the therapeutic dose is tapered over time until the desired maintenance dose is reached. For example, in some embodiments, the first tapered dose is about 50% to about 95% of the therapeutic dose. In some embodiments, the second tapered dose is about 40% to about 90% of the therapeutic dose. In some embodiments, the third tapered dose is about 30% to about 85% of the therapeutic dose. In some embodiments, the fourth tapered dose is about 20% to about 80% of the therapeutic dose. In some embodiments, the fifth tapered dose is about 10% to about 75% of the therapeutic dose. In some embodiments, one tapered dose is given to achieve the maintenance dose. In some embodiments, two tapered doses are given to achieve the maintenance dose. In some embodiments, three tapered doses are given to achieve the maintenance dose. In some embodiments, four or more tapered doses are given to achieve the maintenance dose. Determination of the tapered doses, number of tapered doses, and the like can be readily made a qualified clinician.

In one embodiment, the QT interval is not prolonged more than 30 ms. In a preferred embodiment, the QT interval is not prolonged more than 20 ms.

In some embodiments, the patient is administered periodically, such as once, twice, three time, four times or five time daily with noribogaine or a pharmaceutically acceptable salt or solvate thereof. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made a qualified clinician.

Noribogaine or a pharmaceutically acceptable salt or solvate thereof, suitable for administration in accordance with the methods provide herein, can be suitable for a variety of delivery modes including, without limitation, oral and transdermal delivery. Compositions suitable for internal, pulmonary, rectal, nasal, vaginal, lingual, intravenous, intra-arterial, intramuscular, intraperitoneal, intracutaneous and subcutaneous routes may also be used. Possible dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A. Oslo editor, Easton Pa. 1980).

In a preferred embodiment, noribogaine or a pharmaceutically acceptable salt or solvate thereof is administered orally, which may conveniently be provided in tablet, caplet, sublingual, liquid or capsule form. In certain embodiments, the noribogaine is provided as noribogaine HCl, with dosages reported as the amount of free base noribogaine. In some embodiments, the noribogaine HCl is provided in hard gelatin capsules containing only noribogaine HCl with no excipients.

The patient may suffer from addiction to any opioid or opiate, or opioid-like drug. In a preferred embodiment, the opioid or opioid-like drug is selected from the group consisting of heroin, cocaine, opiate, methadone, morphine, codeine, hydrocodone, oxycodone, and methamphetamine. In one embodiment, the opioid or opioid-like drug is heroin. In one embodiment, the opioid or opioid-like drug is methadone. In one embodiment, the opioid or opioid-like drug is morphine.

Patient Pre-Screening and Monitoring

Pre-screening of patients before treatment with noribogaine and/or monitoring of patients during noribogaine treatment may be required to ensure that QT interval is not prolonged beyond a certain value. For example, QT interval greater than 500 ms can be considered dangerous for individual patients. Pre-screening and/or monitoring may be necessary at high levels of noribogaine treatment.

In a preferred embodiment, a patient receiving a therapeutic dose of noribogaine is monitored in a clinical setting. Monitoring may be necessary to ensure the QT interval is not prolonged to an unacceptable degree. A "clinical setting" refers to an inpatient setting (e.g., inpatient clinic, hospital, rehabilitation facility) or an outpatient setting with frequent, regular monitoring (e.g., outpatient clinic that is visited daily to receive dose and monitoring). Monitoring includes monitoring of QT interval. Methods for monitoring of QT interval are well-known in the art, for example by ECG.

In one embodiment, a patient receiving a maintenance dose of noribogaine is not monitored in a clinical setting. In one embodiment, a patient receiving a maintenance dose of noribogaine is monitored periodically, for example daily, weekly, monthly, or occasionally.

In one aspect, this invention relates to a method for treating opioid or opioid-like drug abuse and/or symptoms of withdrawal in an addicted patient, comprising selecting an opioid- or opioid-like drug-addicted patient who is prescreened to evaluate the patient's expected tolerance for prolongation of QT interval, administering to the patient a dosage of noribogaine or pharmaceutically acceptable salt or solvate thereof that provides an average serum concentration of about 50 ng/mL to about 850 ng/mL (AUC/24 h), said concentration being sufficient to inhibit or ameliorate said abuse or symptoms while maintaining a QT interval of less than 500 ms during said treatment. In some embodiments, the concentration is sufficient to attenuate said abuse or symptoms while maintaining a QT interval of less than about 470 ms during treatment. Preferably, the concentration is sufficient to attenuate said abuse or symptoms while maintaining a QT interval of less than about 450 ms during treatment. In one embodiment, the concentration is sufficient to attenuate said abuse or symptoms while maintaining a QT interval of less than about 420 ms during treatment.

In one embodiment, prescreening of the patient comprises ascertaining that noribogaine treatment will not result in a QT interval over about 500 ms. In one embodiment, prescreening of the patient comprises ascertaining that noribogaine treatment will not result in a QT interval over about 470 ms. In one embodiment, prescreening comprises ascertaining that noribogaine treatment will not result in a QT interval over about 450 ms. In one embodiment, prescreening comprises ascertaining that noribogaine treatment will not result in a QT interval over about 420 ms. In one embodiment, prescreening comprises determining the patient's pre-treatment QT interval.

As it relates to pre-screening or pre-selection of patients, patients may be selected based on any criteria as determined by the skilled clinician. Such criteria may include, by way of non-limiting example, pre-treatment QT interval, pre-existing cardiac conditions, risk of cardiac conditions, age, sex, general health, and the like. The following are examples of selection criteria for disallowing noribogaine treatment or restricting dose of noribogaine administered to the patient: high QT interval before treatment (e.g., such that there is a risk of the patient's QT interval exceeding 500 ms during treatment); congenital long QT syndrome; bradycardia; hypokalemia or hypomagnesemia; recent acute myocardial infarction; uncompensated heart failure; and taking other drugs that increase QT interval. In some embodiments, the methods can include selecting and/or administering/providing noribogaine to a patient that lacks one more of such criteria.

In one embodiment, this invention relates to pre-screening a patient to determine if the patient is at risk for prolongation of the QT interval beyond a safe level. In one embodiment, a patient at risk for prolongation of the QT interval beyond a safe level is not administered noribogaine. In one embodiment, a patient at risk for prolongation of the QT interval beyond a safe level is administered noribogaine at a limited dosage.

In one embodiment, this invention relates to monitoring a patient who is administered a therapeutic dose of noribogaine. In one embodiment, the dose of noribogaine is reduced if the patient has serious adverse side effects. In one embodiment, the noribogaine treatment is discontinued if the patient has serious adverse side effects. In one embodiment, the adverse side effect is a QT interval that is prolonged beyond a safe level. The determination of a safe level of prolongation is within the skill of a qualified clinician.

Kit of Parts

One aspect of this invention is directed to a kit of parts for the treatment of opioid or opioid-like drug abuse and/or symptoms of withdrawal in an addicted patient, wherein the kit comprises a composition comprising noribogaine or salt or solvate thereof and a means for administering the composition to a patient in need thereof. The means for administration to a patient can include, for example, any one or combination of noribogaine, or a noribogaine derivative, or a pharmaceutically acceptable salt or solvate thereof, a transdermal patch, a syringe, a needle, an IV bag comprising the composition, a vial comprising the composition, an inhaler comprising the composition, etc. In one embodiment, the kit of parts further comprises instructions for dosing and/or administration of the composition.

In some aspects, the invention is directed to a kit of parts for administration of noribogaine, the kit comprising multiple delivery vehicles, wherein each delivery vehicle contains a discrete amount of noribogaine and further wherein each delivery vehicle is identified by the amount of noribogaine provided therein; and optionally further comprising a dosing treatment schedule in a readable medium. In some embodiments, the dosing treatment schedule includes the amount of noribogaine required to achieve each average serum level is provided. In some embodiments, the kit of parts includes a dosing treatment schedule that provides an attending clinician the ability to select a dosing regimen of noribogaine based on the sex of the patient, mass of the patient, and the serum level that the clinician desires to achieve. In some embodiments, the dosing treatment schedule further provides information corresponding to the volume of blood in a patient based upon weight (or mass) and sex of the patient. In an embodiment, the storage medium can include an accompanying pamphlet or similar written information that accompanies the unit dose form in the kit. In an embodiment, the storage medium can include electronic, optical, or other data storage, such as a non-volatile memory, for example, to store a digitally-encoded machine-readable representation of such information.

The term "delivery vehicle" as used herein refers to any formulation that can be used for administration of noribogaine to a patient. Non-limiting, exemplary delivery vehicles include caplets, pills, capsules, tablets, powder, liquid, or any other form by which the drug can be administered.

Delivery vehicles may be intended for administration by oral, inhaled, injected, or any other means.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

In some aspects, the machine-readable medium comprises software that contains information regarding dosing schedules for the unit dose form of noribogaine and optionally other drug information. In some embodiments, the software may be interactive, such that the attending clinician or other medical professional can enter patient information. In a non-limiting example, the medical professional may enter the weight and sex of the patient to be treated, and the software program provides a recommended dosing regimen based on the information entered. The amount and timing of noribogaine recommended to be delivered will be within the dosages that result in the serum concentrations as provided herein.

In some embodiments, the kit of parts comprises multiple delivery vehicles in a variety of dosing options. For example, the kit of parts may comprise pills or tablets in multiple dosages, such as 240 mg, 120 mg, 90 mg, 60 mg, 30 mg, 20 mg, and/or 10 mg of noribogaine per pill. Each pill is labeled such that the medical professional and/or patient can easily distinguish different dosages. Labeling may be based on printing or embossing on the pill, shape of the pill, color of pill, the location of the pill in a separate, labeled compartment within the kit, and/or any other distinguishing features of the pill. In some embodiments, all of the delivery vehicles within a kit are intended for one patient. In some embodiments, the delivery vehicles within a kit are intended for multiple patients.

One aspect of this invention is directed to a kit of parts for the treatment of opioid, or opioid-like drug, abuse and/or symptoms of withdrawal in an addicted patient, wherein the kit comprises a unit dose form of noribogaine or salt or solvate thereof. The unit dose form provides a patient with an average serum level of noribogaine of from about 50 ng/mL to about 800 ng/mL or about 60 ng/mL to about 800 ng/mL.

In some embodiments, the unit dose form comprises one or multiple dosages to be administered periodically, such as once, twice, three time, four times or five time daily with noribogaine or its prodrug. In some embodiments, the administration is once daily, or once every second day, once every third day, three times a week, twice a week, or once a week. The dosage and frequency of the administration depends on criteria including the route of administration, content of composition, age and body weight of the patient, condition of the patient, sex of the patient, without limitation, as well as by the severity of the addiction. Determination of the unit dose form providing a dosage and frequency suitable for a given patient can readily be made by a qualified clinician.

These dose ranges may be achieved by transdermal, oral, or parenteral administration of noribogaine or a pharmaceutically acceptable salt or solvate thereof in unit dose form. Such unit dose form may conveniently be provided in transdermal patch, tablet, caplet, liquid or capsule form. In certain embodiments, the noribogaine is provided as noribogaine HCl, with dosages reported as the amount of free base noribogaine. In some embodiments, the noribogaine HCl is provided in hard gelatin capsules containing only noribogaine HCl with no excipients. In some embodiments, noribogaine is provided in saline for intravenous administration.

Formulations

This invention further relates to pharmaceutically acceptable formulations comprising a unit dose of noribogaine or pharmaceutically acceptable salt or solvate thereof, wherein the amount of noribogaine is sufficient to provide an average serum concentration of about 50 ng/mL to about 850 ng/mL (AUC/24 h) when administered to a patient. In a preferred embodiment, the amount of noribogaine is sufficient to provide an average serum concentration of about 50 ng/mL to about 400 ng/mL (AUC/24 h) when administered to a patient.

In some embodiments, the unit dose of noribogaine is administered in one or more dosings.

In one embodiment, the amount of noribogaine is sufficient to provide an average serum concentration of noribogaine from about 50 ng/mL to about 800 ng/mL or about 60 ng/mL to about 800 ng/mL. In one embodiment, the amount of noribogaine is sufficient to provide an average serum concentration of noribogaine from about 50 ng/mL to about 700 ng/mL or about 60 ng/mL to about 700 ng/mL. In one embodiment, the amount of noribogaine is sufficient to provide an average serum concentration of noribogaine from about 50 ng/mL to about 600 ng/mL, or about 60 ng/mL to about 600 ng/mL. In a preferred embodiment, the amount of noribogaine is sufficient to provide an average serum concentration of noribogaine from about 50 ng/mL to about 500 ng/mL, or about 60 ng/mL to about 500 ng/mL. In one embodiment, the amount of noribogaine is sufficient to provide an average serum concentration of noribogaine from about 50 ng/mL to about 400 ng/mL, or about 60 ng/mL to about 400 ng/mL. In one embodiment, the amount of noribogaine is sufficient to provide an average serum concentration of noribogaine from about 50 ng/mL to about 300 ng/mL, or about 60 ng/mL to about 300 ng/mL. In one embodiment, the amount of noribogaine is sufficient to provide an average serum concentration of noribogaine from about 50 ng/mL to about 200 ng/mL, or about 60 ng/mL to about 200 ng/mL. In one embodiment, the amount of noribogaine is sufficient to provide an average serum concentration of noribogaine from about 50 ng/mL to about 100 ng/mL, or about 60 ng/mL to about 100 ng/mL. The ranges include both extremes as well as any subranges between.

In some embodiments, the formulation is designed for periodic administration, such as once, twice, three time, four times or five time daily with noribogaine or a pharmaceutically acceptable salt or solvate thereof. In some embodiments, the administration is once daily, or once every second day, once every third day, three times a week, twice a week, or once a week. The dosage and frequency of the administration depends on the route of administration, content of composition, age and body weight of the patient, condition of the patient, without limitation. Determination of dosage and frequency suitable for the present technology can be readily made a qualified clinician.

In some embodiments, the formulation designed for administration in accordance with the methods provide herein can be suitable for a variety of delivery modes including, without limitation, oral and transdermal delivery. Formulations suitable for internal, pulmonary, rectal, nasal, vaginal, lingual, intravenous, intra-arterial, intramuscular, intraperitoneal, intracutaneous and subcutaneous routes may also be used. Possible formulations include tablets, capsules, pills, powders, aerosols, suppositories, parenterals, and oral liquids, including suspensions, solutions and emulsions. Sustained release dosage forms may also be used. All formulations may be prepared using methods that are standard in the art (see e.g., Remington's Pharmaceutical Sciences, 16th ed., A. Oslo editor, Easton Pa. 1980).

In a preferred embodiment, the formulation is designed for oral administration, which may conveniently be provided in tablet, caplet, sublingual, liquid or capsule form. In certain embodiments, the noribogaine is provided as noribogaine HCl, with dosages reported as the amount of free base noribogaine. In some embodiments, the noribogaine HCl is provided in hard gelatin capsules containing only noribogaine HCl with no excipients.

EXAMPLES

The following Examples are intended to further illustrate certain embodiments of the disclosure and are not intended to limit its scope.

Example 1

Pharmacokinetics and Pharmacodynamics of Noribogaine in Humans

Thirty-six healthy, drug-free male volunteers, aged between 18-55 years, were enrolled in and completed the study. This was an ascending single-dose, placebo-controlled, randomized double blind, parallel group study. Mean (SD) age was 22.0 (3.3) years, mean (SD) height was 1.82 (0.08) m, and mean (SD) weight was 78.0 (9.2) kg. Twenty-six subjects were Caucasian, 3 were Asian, 1 Maori, 1 Pacific Islander, and 5 Other. The protocol for this study was approved by the Lower South Regional Ethics Committee (LRS/12/06/015), and the study was registered with the Australian New Zealand Clinical Trial Registry (ACTRN12612000821897). All subjects provided signed informed consent prior to enrolment, and were assessed as suitable to participate based on review of medical history, physical examination, safety laboratory tests, vital signs and ECG.

Within each dose level, 6 participants were randomized to receive noribogaine and 3 to receive placebo, based on a computer-generated random code. Dosing began with the lowest noribogaine dose, and subsequent cohorts received the next highest dose after the safety, tolerability, and blinded pharmacokinetics of the completed cohort were reviewed and dose-escalation approved by an independent Data Safety Monitoring Board. Blinded study drug was administered as a capsule with 240 ml of water after an overnight fast of at least 10 hours. Participants did not receive any food until at least 5 hours post-dose. Participants were confined to the study site from 12 hours prior to drug administration, until 72 hours post-dose, and there were subsequent outpatient assessments until 216 hours post-dose.

Blood was obtained for pharmacokinetic assessments pre-dose and then at 0.25, 0.5, 0.75, 1.0, 1.25, 1.5, 2, 2.5, 3, 3.5, 4, 4.5, 5, 5.5, 6, 7, 8, 10, 12, 14, 18, 24, 30, 36, 48, 60, 72, 96, 120, 168 and 216 hours post-dose. Samples were centrifuged and plasma stored at −70° C. until analyzed. Block 24 hour urine collections were obtained following study drug administration for the 30 and 60 mg cohorts. Aliquots were frozen at −20° C. until analyzed.

Pulse oximetry and capnography data were collected continuously using a GE Carescape B650 monitoring system from 2 hours prior to dosing and until six hours after dosing, and thereafter at 12, 24, 48 and 72 hours post-dosing. Additional oximetry data were collected at 120, 168 and 216 hours. Pupillary miosis was assessed by pupillometry. Dark-adapted pupil diameter was measured in triplicate using a Neuroptics PLR-200 pupillometer under standardized light intensity (<5 lux) pre-dose, and at 2, 4, 6, 12, 24, 48, 72, 96, 120, 168 and 216 hours post-dosing.

Plasma noribogaine concentrations were determined in the 3 mg and 10 mg dose groups using a validated, sensitive LCMSMS method. Sample preparation involved double extraction of basified plasma samples with tert-butyl methyl ether, drying the samples under a stream of nitrogen and reconstitution of sample with acetonitrile:B.P. water (5:95, v/v) containing 0.1% (v/v) formic acid. The compounds were separated by a 150×2.0 mm Luna 5 μm C18 column and detected with a triple—quadrupole API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, and for the internal standard noribogaine-$d_4$ m/z 301.1→122.2. Analyst® software was used for data acquisition and processing. The ratio of the peak area of noribogaine to the internal standard noribogaine-$d_4$ was used for calibration and measurement of the unknown concentration of noribogaine. The lower limit of quantification (LLOQ) was 0.025 ng/ml noribogaine. The calibration curve was between 0.025 and 25.600 ng/ml noribogaine. Mobile phase A was acetonitrile:B.P. water (5:95, v/v) containing 0.1% (v/v) formic acid, and mobile phase B was acetonitrile:B.P. water (95:5, v/v) containing 0.1% (v/v) formic acid. Total run time was 6 minutes. Binary flow: Initial concentration was 8% mobile phase B; hold at 8% mobile phase B for 0.5 minutes and linear rise to 90% mobile phase B over 1.5 minutes; hold at 90% mobile phase B for 1 minute and then drop back to 8% mobile phase B over 0.01 minute. Equilibrate system for 3 minutes. Total run time was 6 minutes. Within- and between-day assay precision was <9%, and within- and between-day assay accuracy was <9%.

Plasma noribogaine concentrations were determined in the 30 mg and 60 mg dose groups using a validated, sensitive LCMSMS method. Sample preparation involved deproteinization of plasma samples with acetonitrile and dilution of sample with 0.1% (v/v) formic acid. The compounds were separated by a 150×2.0 mm Luna 5 μm C18 column and detected with a triple—quadrupole API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, and for the internal standard noribogaine-$d_4$ m/z 301.1→122.2. Analyst® software was used for data acquisition and processing. The ratio of the peak area of noribogaine to the internal standard noribogaine-$d_4$ was used for calibration and measurement of the unknown concentration of noribogaine. The LLOQ was 0.50 ng/ml noribogaine. The calibration curve was between 0.50 and 256.00 ng/ml noribogaine. Mobile phase was the same as method A, and binary flow was also the same as method A. The within- and between-day assay precision was <9%, and the within- and between-day assay accuracy was <9%.

Plasma noribogaine glucuronide concentrations were determined in the 30 mg and 60 mg dose groups using a validated sensitive LCMSMS method. Sample preparation involved deproteinization of plasma samples with acetonitrile, drying the samples under a stream of nitrogen and reconstitution of sample with acetonitrile:B.P. water (5:95, v/v) containing 0.1% (v/v) formic acid. The compounds were separated by a 150×2.0 mm Luna 5 μm C18 column and detected with a triple—quadrupole API 4000 or 5000 mass spectrometer using electrospray ionization in positive mode and multiple reaction monitoring. Noribogaine-$d_4$ was used as the internal standard. The precursor-product ion transition values for noribogaine glucuronide were m/z 472.8→297.3, and for the internal standard noribogaine-$d_4$ m/z 301.1→122.2. Analyst® software was used for data acquisition and processing. The ratio of the peak area of noribogaine glucuronide to the internal standard noribogaine-$d_4$ was used for calibration and measurement of the unknown concentration of noribogaine glucuronide. The LLOQ was 0.050 ng/ml noribogaine glucuronide. The calibration curve was between 0.050 and 6.400 ng/ml noribogaine glucuronide. Mobile phases was the same as method A. Binary flow: Initial concentration was 6% mobile phase B; hold at 6% mobile phase B for 0.5 minutes and linear rise to 90% mobile phase B over 2 minutes; hold at 90% mobile phase B for 1 minute and then drop back to 6% mobile phase B over 0.01 minute. Equilibrate system for 3.5 minutes. Total run time was 7 minutes. The within- and between-day assay precision was <11%, and the within- and between-day assay accuracy was <10%.

Urine noribogaine and noribogaine glucuronide concentrations were determined in the 30 mg and 60 mg dose groups using a validated sensitive LCMSMS method. Sample preparation involved deproteinization of urine samples with acetonitrile and dilution of the sample with 0.1% (v/v) formic acid. The compounds were separated by a 150×2.0 mm Luna 5 μm C18 column and detected with a triple—quadrupole API 5000 mass spectrometer using electrospray ionization in positive mode and multiple reaction monitoring. Noribogaine-$d_4$ was used as the internal standard. The precursor-product ion transition values for noribogaine were m/z 297.6→122.3, noribogaine glucuronide m/z 472.8→297.3, and for the internal standard noribogaine-$d_4$ m/z 301.1→122.2. Analyst® software was used for data acquisition and processing. The ratios of the peak area of noribogaine and noribogaine glucuronide to the internal standard noribogaine-$d_4$ were used for calibration and measurement of the unknown concentration of noribogaine and its glucuronide. Assay LLOQ was 20.0 ng/ml for noribogaine and 2.0 ng/ml for noribogaine glucuronide. The calibration curve was between 20.0 and 5120.0 ng/ml noribogaine, and 2.0 and 512.0 ng/ml noribogaine glucuronide. Mobile phases were as described in method A, and binary flow as in method C. The within- and between-day assay precision was <13%, and within- and between-day assay accuracy was <12%.

Noribogaine and noribogaine glucuronide concentrations above the limit of quantification were used to calculate pharmacokinetic parameters using model-independent methods. The maximum plasma concentration (Cmax) and time to maximum plasma concentration (Tmax) were the observed values. Plasma concentration data in the post-distribution phase of the plasma concentration-time plot were fitted using linear regression to the formula ln C=ln Co−t.Kel, where Co was the zero-time intercept of the extrapolated terminal phase and Kel was the terminal elimination rate constant. The half-life ($t_{1/2}$) was determined using the formula $t_{1/2}$=0.693/Kel. The area under the concentration-time curve (AUC) from time zero to the last determined concentration-time point (tf) in the post distribution phase was calculated using the trapezoidal rule. The area under the curve from the last concentration-time point in the post distribution phase (Ctf) to time infinity was calculated from $AUC_{t-\infty}$=Ctf/Kel. The concentration used for Ctf was the last determined value above the LLOQ at the time point. The total $AUC_{0-\infty}$ was obtained by adding $AUC_{tf}$ and $AUC_{t-\infty}$. Noribogaine apparent clearance (CL/F) was determined using the formula CL/F=Dose/$AUC_{0-\infty}$×1000, and apparent volume of distribution (Vd/F) was determined using the formula Vd/F=(CL/F)/Kel. Total urine noribogaine was the sum of both analytes.

Summary statistics (means, standard deviations, and coefficients of variation) were determined for each dose group for safety laboratory test data, ECG and pharmacokinetic parameters, and pharmacodynamic variables. Categorical variables were analysed using counts and percentages. Dose-proportionality of AUC and Cmax was assessed using linear regression. The effect of dose on pharmacodynamic parameter values over time was assessed using two-factor analysis of variance (ANOVA). Pairwise comparisons (with Tukey-Kramer adjustment) between each dose group to the placebo were conducted at each time point using the least squares estimates obtained from the ANOVA, using SAS Proc Mixed (SAS ver 6.0).

Results

Pharmacokinetics: Mean plasma concentration-time plots of noribogaine are shown in FIG. 1, and mean pharmacokinetic parameters are shown in Table 1.

TABLE 1

| Noribogaine | 3 mg (n = 6) (mean (SD)) | 10 mg (n = 6) (mean (SD)) | 30 mg (n = 6) (mean (SD)) | 60 mg (n = 6) (mean (SD) |
|---|---|---|---|---|
| $AUC_{0-\infty}$ (ng · hr/ml) | 74.2 (13.1) | 254.5 (78.9) | 700.4 (223.3) | 1962.2 (726.5) |
| $AUC_{0-216}$ (ng · hr/ml) | 72.2 (13.2) | 251.4 (78.5) | 677.6 (221.1) | 1935.4 (725.4) |
| Cmax (ng/ml) | 5.2 (1.4) | 14.5 (2.1) | 55.9 (14.8) | 116.0 (22.5) |
| Tmax (hr) | 1.9 (0.6) | 2.9 (1.8) | 1.8 (0.6) | 2.4 (0.6) |
| $t_{1/2}$ (hr) | 40.9 (8.7) | 49.2 (11.5) | 27.6 (7.0)) | 29.1 (9.3) |
| Vd/F (L) | 2485.1 (801.5) | 3085.8 (1197.0) | 1850.8 (707.9) | 1416.8 (670.1) |
| CL/F (L/h) | 41.4 (7.0) | 42.3 (12.0) | 46.9 (16.4) | 34.0 (11.4) |
| Noribogaine glucuronide | | | | |
| $AUC_{0-\infty}$ (ng · hr/ml) | — | — | 25.8 (9.3) | 67.1 (21.9) |
| $AUC_{0-216}$ (ng · hr/ml) | — | — | 25.7 (9.1) | 65.0 (21.5) |
| Cmax (ng/ml) | — | — | 1.8 (0.6) | 4.1 (1.2) |

TABLE 1-continued

| Noribogaine | 3 mg (n = 6) (mean (SD)) | 10 mg (n = 6) (mean (SD)) | 30 mg (n = 6) (mean (SD)) | 60 mg (n = 6) (mean (SD) |
|---|---|---|---|---|
| Tmax (hr) | — | — | 3.0 (0.6) | 3.8 (1.2) |
| $t_{1/2}$ (hr) | — | — | 20.6 (4.9) | 23.1 (3.0) |

Noribogaine was rapidly absorbed, with peak concentrations occurring 2-3 hours after oral dosing. Fluctuations in individual distribution-phase concentration-time profiles may suggest the possibility of enterohepatic recirculation (see highlighted individual 4-8 hour profiles in FIG. 1, insert). Both Cmax and AUC increased linearly with dose (Table 1, upper panel). Mean half-life estimates of 28-50 hours were observed across dose groups for noribogaine. Volume of distribution was extensive (1417-3086 L across dose groups).

Figure 2:
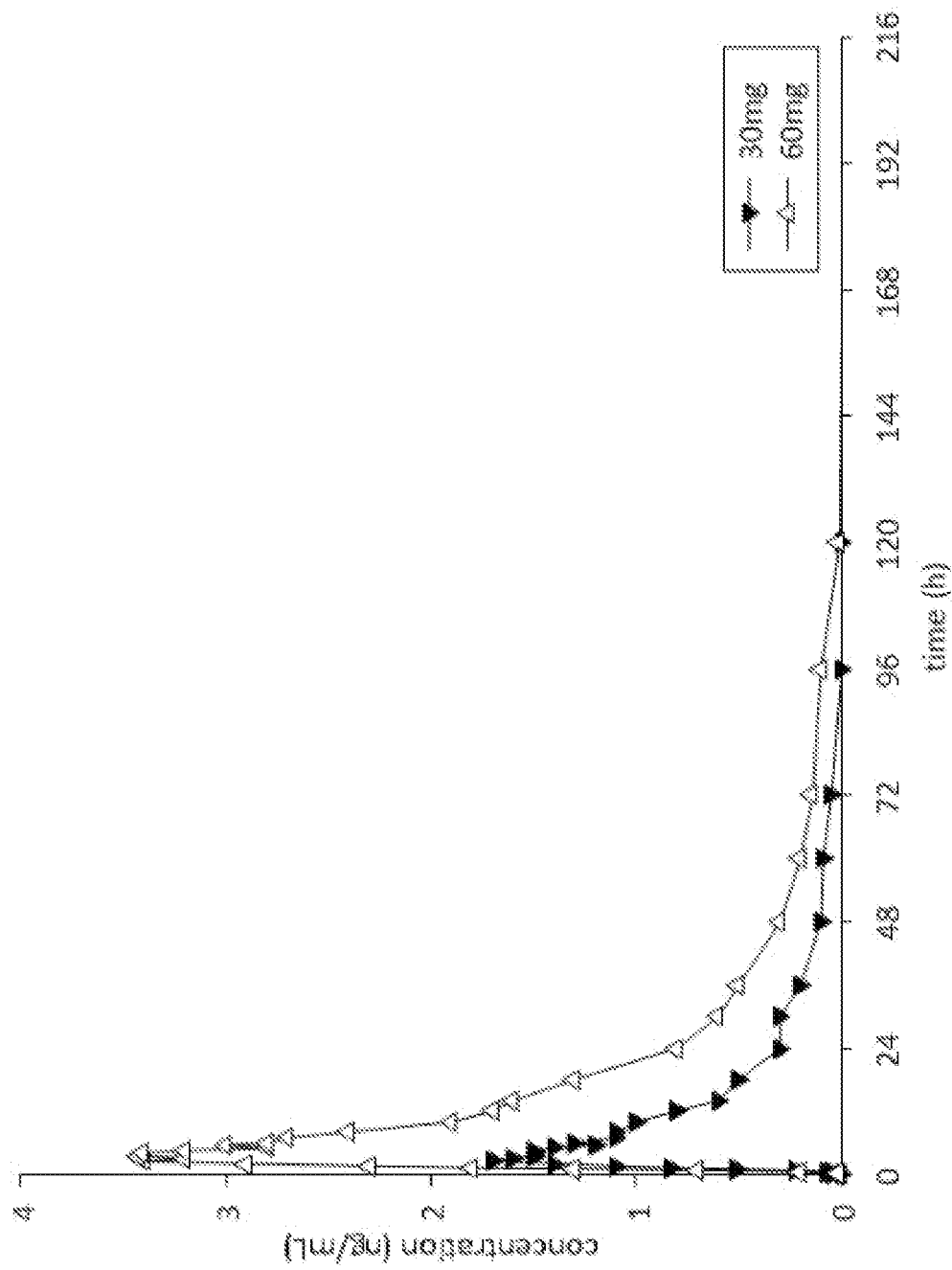
FIG. 2 represents mean plasma noribogaine glucuronide concentration-time profiles in healthy patients after single oral 30 or 60 mg doses.

Mean plasma noribogaine glucuronide concentration-time plots for the 30 mg and 60 mg dose group are shown in FIG. 2, and mean pharmacokinetic parameters are shown in Table 1, lower panel. Noribogaine glucuronide was detected in all subjects by 0.75 hours, with peak concentrations occurring 3-4 hours after noribogaine dosing. Mean half-life of 21-23 hours was estimated for plasma noribogaine glucuronide. The proportion of noribogaine glucuronide Cmax and AUC relative to noribogaine was 3-4% for both dose groups. Total urine noribogaine elimination was 1.16 mg and 0.82 mg for the 30 mg and 60 mg dose groups respectively, representing 3.9% and 1.4% of the doses administered.

Pharmacodynamics: There was no evidence of pupillary constriction in subjects dosed with noribogaine. No between-dose group differences in pupil diameter were detected over time. After adjusting for baseline differences, comparison of each dose group with placebo by ANOVA showed no statistically significant differences (p>0.9).

Noribogaine treatment showed no analgesic effect in the cold pressor test. Analgesic effect was assessed based on duration of hand immersion in ice water and on visual analog scale (VAS) pain scores upon hand removal from the water bath. For duration of hand immersion, after adjusting for baseline differences, comparison of each dose group with placebo by ANOVA showed no statistically significant differences (p>0.9). Similarly, for VAS pain scores, after adjusting for baseline differences, comparison of each dose group with placebo by ANOVA showed no statistically significant differences (p=0.17).

Example 2

Safety and Tolerability of Noribogaine in Humans

Safety and tolerability of noribogaine were tested in the group of volunteers from Example 1. Cold pressor testing was conducted in 1° C. water according to the method of Mitchell et al. (*J Pain* 5:233-237, 2004) pre-dose, 6, 24, 48, 72 and 216 hours post-dosing. Safety evaluations included clinical monitoring, recording of adverse events (AEs), safety laboratory tests, vital signs, ECG telemetry from −2 h to 6 h after dosing, and 12-lead electrocardiograms (ECGs) up to 216 hours post-dosing.

Results

A total of thirteen adverse events were reported by seven participants (Table 2). Six adverse events were reported by three participants in the placebo group, five adverse events were reported by two subjects in the 3 mg dose group, and one adverse event was reported by single subjects in the 10 mg and 30 mg dose groups, respectively. The most common adverse events were headache (four reports) and epistaxis (two reports). All adverse events were of mild-moderate intensity, and all resolved prior to study completion. There were no changes in vital signs or safety laboratory tests of note. In particular, there were no changes in oximetry or capnography, or changes in respiratory rate. There were no QTcF values >500 msec at any time. One subject dosed with 10 mg noribogaine had a single increase in QTcF of >60 msec at 24 hours post-dosing.

TABLE 2

| Dose (mg) | Mild | Moderate | Severe |
|---|---|---|---|
| Placebo | Blepharitis<br>Bruising<br>Dry Skin<br>Eye pain, nonspecific<br>Infection at cannula site | Epistaxis | — |
| 3 | Back pain<br>Dizziness<br>Epistaxis<br>Headache | Headache | — |
| 10 | Headache | — | — |
| 30 | Headache | — | — |
| 60 | — | — | — |

Example 3

Efficacy of Noribogaine in Humans

The efficacy of noribogaine in humans was evaluated in opioid-dependent participants in a randomized, placebo-controlled, double-blind trial. Patients had been receiving methadone treatment as the opioid substitution therapy, but were transferred to morphine treatment prior to noribogaine administration. This was done to avoid negative noribogaine-methadone interactions that are not observed between noribogaine and methadone. See U.S. Provisional Application Ser. No. 61/852,485, filed Mar. 15, 2013, which is incorporated herein by reference in its entirety.

In the first cohort, six patients were orally administered a single dose of 60 mg noribogaine, and three patients received placebo. In the second cohort, five patients were orally administered a single dose of 120 mg noribogaine, and three patients received placebo. Treatment was administered 2 hours after last morphine dose and the time to resumption of morphine (opioid substitution treatment, OST) was determined. No adverse effects of noribogaine were observed in any of the participants, including no hallucinatory effects.

Figure 3:
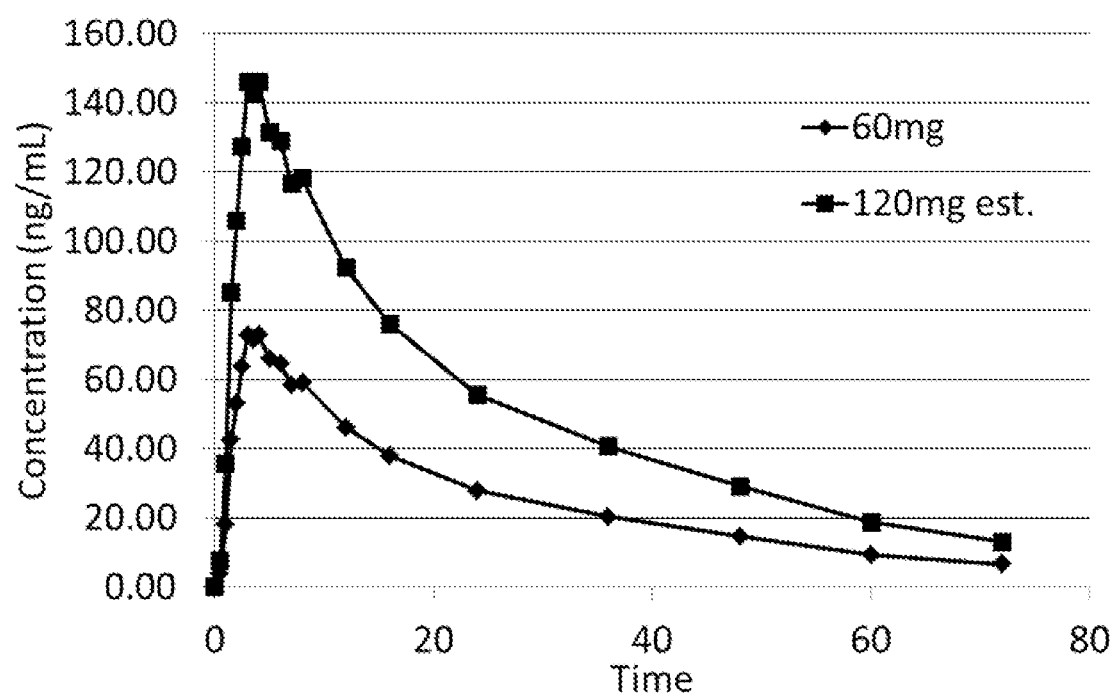
FIG. 3 illustrates the mean noribogaine concentration-time profile in opioid-addicted patients after a single oral 60 mg dose of noribogaine (gray diamonds). Mean noribogaine concentration-time profile in opioid-addicted patients after single oral 120 mg dose of noribogaine (black squares) was estimated based on values for patients receiving 60 mg dose.

FIG. 3 indicates the serum noribogaine concentration over time. Serum concentrations for 120 mg dose (black squares) are estimated based on data from the 60 mg dose (gray diamonds).

Blinded Results

Figure 4A:
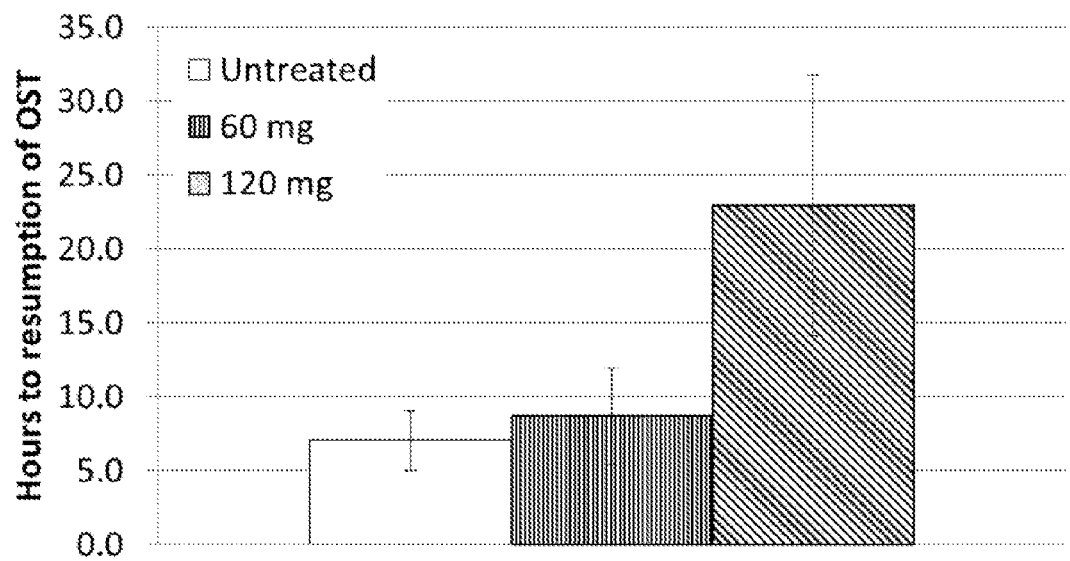
FIG. 4A illustrates hours to resumption of opioid substitution treatment in patients given no treatment (light gray bar), or a single oral dose of noribogaine or placebo (60 mg, dark gray bar; 120 mg, black bar). Error bars represent standard deviation.

Patients in the first cohort exhibited an average time to resumption of opioids after treatment with 60 mg noribogaine or placebo of approximately 8.7 hours, which is almost 2 hours longer than that reported for untreated patients in a similar study. Patients in the second cohort exhibited an average time to resumption of opioids after treatment with 120 mg noribogaine or placebo of approximately 23 hours. FIG. 4A indicates the average time to resumption of morphine for control (untreated, light gray bar), first cohort (dark gray bar) and second cohort (black bar). Mean prolongation of the QT interval was less than 10 ms for patients in the first cohort and was less than 40 ms in the second cohort.

Figure 4B:
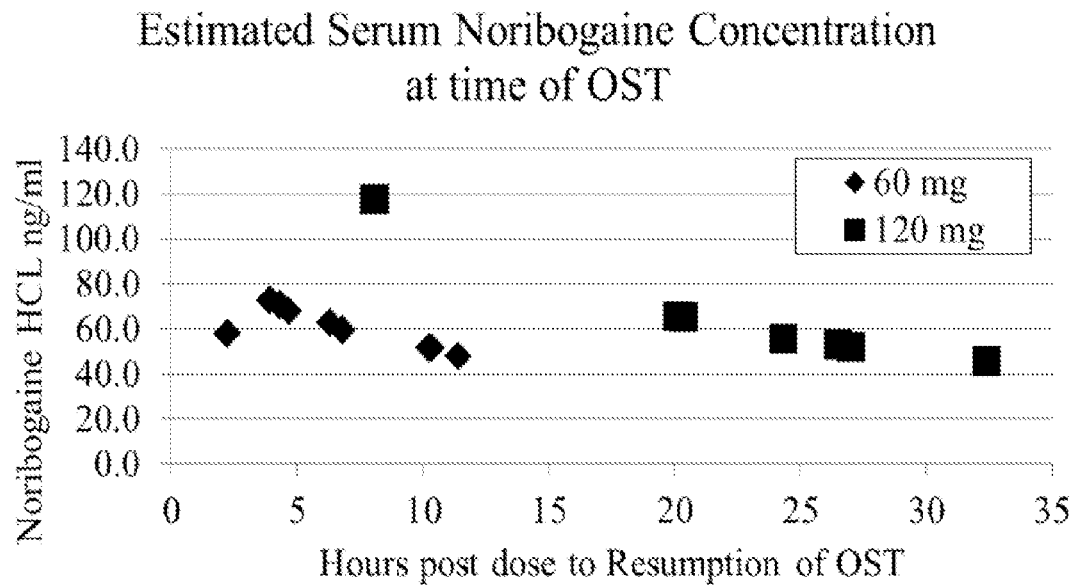
FIG. 4B illustrates the estimated serum noribogaine concentration in ng/mL at time of resumption of opioid substitution treatment (OST) in patients receiving single oral dose of noribogaine or placebo (60 mg, dark gray diamonds; 120 mg, black squares). Data is estimated based on the concentration-time profile in FIG. 3.

FIG. 4B indicates the estimated noribogaine concentration (based on the data from FIG. 3) at the time of resumption of morphine for each patient.

Figure 5A:
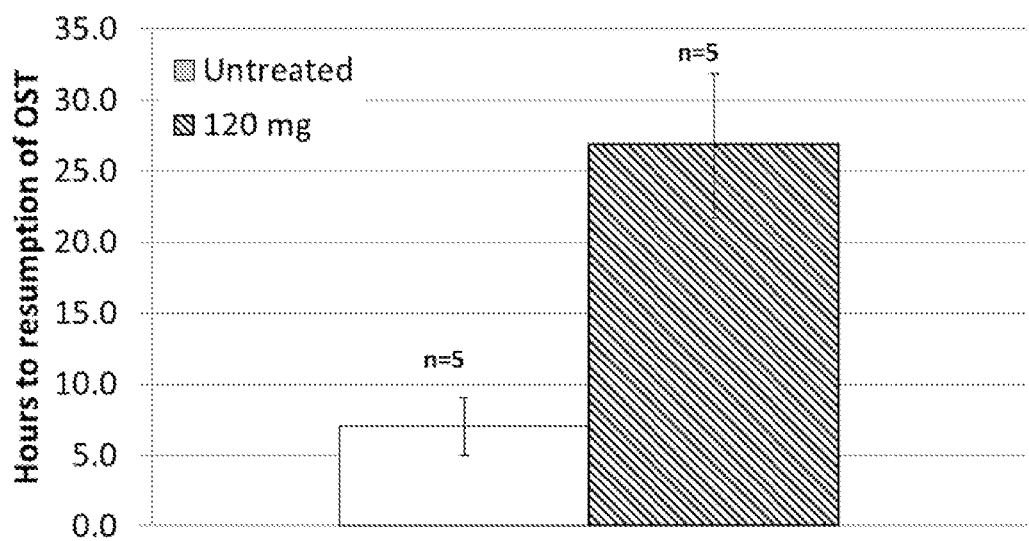
FIG. 5A illustrates imputed results of noribogaine treated patients wherein the results represent hours to resumption of OST in patients given no treatment (light gray bar), or a (imputed) single 120 mg dose of noribogaine (black bar). Error bars represent standard deviation.
Figure 5B:
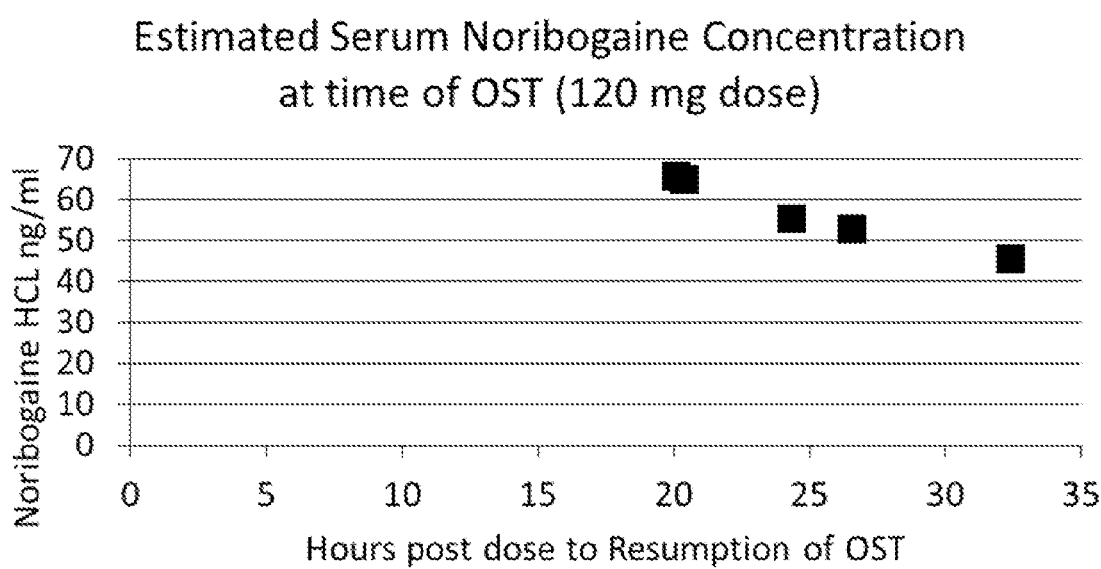
FIG. 5B illustrates imputed results of noribogaine treated patients wherein the results represent the estimated serum noribogaine concentration in ng/mL at time of resumption of OST in patients receiving a (imputed) single oral 120 mg dose of noribogaine (black squares). Data is estimated based on the concentration-time profile in FIG. 3.

Although the study was blinded, the three patients in the second cohort who received placebo were construed to be those patients exhibiting no prolongation of the QT interval. The average time to resumption of OST for the remaining five patients was determined to be approximately 26.8 hours, as indicated in FIG. 5A (black bar). FIG. 5B indicates the estimated noribogaine concentration (based on the data from FIG. 3) at the time of resumption of morphine for each (presumed) noribogaine-treated patient. FIG. 5B demonstrates that, as serum concentrations of noribogaine reach an estimated level of 50 to 60 ng/mL, significant withdrawal symptoms return such that the patient is forced to resume OST. At serum noribogaine levels above about 50 to 60 ng/mL, the patients did not exhibit withdrawal symptoms or those symptoms had not become acute.

What is claimed is:

1. A method for treating opioid or opioid-like drug abuse in a human patient addicted thereto, comprising administering to the patient an aggregate dosage of noribogaine or pharmaceutically acceptable salt or solvate thereof that provides an average serum concentration of about 50 ng/mL to about 500 ng/mL, said concentration being sufficient to inhibit or ameliorate said abuse while targeting a maximum QT interval prolongation of less than about 40 milliseconds during said treatment, wherein the aggregate dosage of noribogaine or pharmaceutically acceptable salt or solvate thereof is from about 60 mg to about 120 mg per day.

2. The method of claim 1, wherein the aggregate dosage of noribogaine or pharmaceutically acceptable salt or solvate thereof is administered as a single dose or multiple doses.

3. The method of claim 1, wherein the aggregate dosage of noribogaine or pharmaceutically acceptable salt or solvate thereof is about 120 mg per day.

4. The method of claim 1, wherein the aggregate dosage of noribogaine or pharmaceutically acceptable salt or solvate thereof provides an average serum concentration of about 50 ng/mL to about 200 ng/mL.

5. The method of claim 1, wherein the QT interval prolongation provides for a QT interval to be maintained at less than about 470 milliseconds during said treatment.

6. The method of claim 5, wherein the patient's QT interval is maintained at less than about 450 milliseconds during said treatment.

7. The method of claim 1, further comprising selecting an addicted patient who is prescreened to evaluate tolerance for prolongation of QT interval.

8. The method of claim 7, wherein the prescreening step comprises ascertaining that noribogaine treatment will not result in a QT interval greater than about 500 milliseconds.

9. The method of claim 8, wherein the prescreening step comprises ascertaining that noribogaine treatment will not result in a QT interval greater than about 470 milliseconds.

10. The method of claim 8, wherein the prescreening step comprises ascertaining that noribogaine treatment will not result in a QT interval greater than about 450 milliseconds.

11. A method for attenuating withdrawal symptoms in a human patient susceptible to such symptoms due to opioid or opioid-like drug addiction, comprising administering to the patient an aggregate dosage of noribogaine or pharmaceutically acceptable salt or solvate thereof that provides an average serum concentration of about 50 ng/mL to about 400 ng/mL, said concentration being sufficient to attenuate said symptoms while targeting a maximum QT interval prolongation of less than about 40 milliseconds during said treatment, wherein the aggregate dosage of noribogaine or pharmaceutically acceptable salt or solvate thereof is from about 60 mg to about 120 mg per day.

12. The method of claim 11, wherein the withdrawal symptoms are due to acute withdrawal.

13. The method of claim 11, wherein the aggregate dosage of noribogaine or pharmaceutically acceptable salt or solvate thereof is administered as a single dose or multiple doses.

14. The method of claim 11, wherein the aggregate dosage of noribogaine or pharmaceutically acceptable salt or solvate thereof is about 120 mg per day.

15. The method of claim 11, wherein the QT interval prolongation provides for a QT interval to be maintained at less than about 470 milliseconds during said treatment.

16. The method of claim 15, wherein the patient's QT interval is maintained at less than about 450 milliseconds during said treatment.

* * * * *